United States Patent
Bell et al.

(10) Patent No.: US 6,544,442 B1
(45) Date of Patent: Apr. 8, 2003

(54) METHOD OF LOADING ORGANIC MATERIALS WITH GROUP III PLUS LANTHANIDE AND ACTINIDE ELEMENTS

(75) Inventors: Zane W. Bell, Oak Ridge, TN (US); Chuen Huei-Ho, Oak Ridge, TN (US); Gilbert M. Brown, Knoxville, TN (US); Charles Hurlbut, Sweetwater, TX (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/400,796

(22) Filed: Sep. 22, 1999

(51) Int. Cl.$^7$ .................... C09K 11/04; C09K 11/06; C07F 9/535
(52) U.S. Cl. ............ 252/478; 252/301.17; 252/301.18; 252/301.35; 252/646; 252/625; 250/518
(58) Field of Search ................... 252/625, 478, 252/301.17, 301.18, 301.35; 250/518; 376/901

(56) References Cited

U.S. PATENT DOCUMENTS

| | | | | |
|---|---|---|---|---|
| 3,514,267 A | * | 5/1970 | Sherrington | |
| 3,640,888 A | * | 2/1972 | Bayarz et al. | 252/301 R |
| 4,176,096 A | * | 11/1979 | Zach | 252/478 |
| 4,259,229 A | * | 3/1981 | Nikitin et al. | |
| 4,795,910 A | * | 1/1989 | Henderson et al. | 250/483.1 |
| 4,891,163 A | * | 1/1990 | Tanaka et al. | 252/627 |

FOREIGN PATENT DOCUMENTS

| | | | | |
|---|---|---|---|---|
| JP | 61 062588 A | * | 9/1984 | |
| JP | 62 061043 A | * | 3/1987 | |
| JP | 0200659 A | * | 6/1988 | |
| SU | 349273 A | * | 4/1974 | |
| SU | 560194 A | * | 7/1977 | |

OTHER PUBLICATIONS

Aleshin, et al., "Plastic Scintillator of High Transparency Containing Gadolinium", *Inst. & Experimental Techniques* 20 #4 pt. 1 997(1977).

Aoyama, et al., "A Neutrom Detector Using Silicon PIN Photodiodes for Personal Neutron Dosimetry", *Nuclear Instruments and Methods in Physics Research* A314:590–594 (1992).

Blank, et al., "X–Ray Fluorescence Control of the Gadolinium Contents of Plastic Scintillators Based on Poly(m-ethylmethacrylate)," J. Anal. Chem. U.S.S.R. 42#2:292 (1987).

Czirr, "Gd–Loaded Plastic Scintillator", *Nuclear Instruments and Methods* 108:613 (1973).0.

Gunder, et al., "Plastic Scintillators with Increased Transparency ", *Inst. & Experimental Tech*.

Harms, et al., "Esotopic Conversion in Gadolinium–Exposure Neutron Imaging", *Nuclear Instruments and Methods* 118:583–587 (1974).

Jeavons, et al., "A New Position–Sensitive Detector for Thermal and Epithermal Neutrons", *Nuclear Instruments and Methods* 148: 29–33 (1978).

Kurata, et al., "Scintillation Characteristics of GSO Single Crystal Grown Under O2–Containing Atmosphere", *IEEE Transactions on Nuclear Science*, vol. 42:1038–1040 (1995).

Reeder, "Neutron Detection Using GSO Scintillator", *Nuclear Instruments & Methods n Physics Research* A 340:371–378 (1994).

"What's a Gadolinium–Loaded Plastic Scintillator?" in Energy Systems News, vol. 1 No. 13 Aug. 5, 1999.

* cited by examiner

Primary Examiner—Margaret Medley
(74) Attorney, Agent, or Firm—Akerman Senterfitt

(57) ABSTRACT

Disclosed is a composition of matter comprising a tributyl phosphate complex of a group 3, lanthanide, actinide, or group 13 salt in an organic carrier and a method of making the complex. These materials are suitable for use in solid or liquid organic scintillators, as in x-ray absorption standards, x-ray fluorescence standards, and neutron detector calibration standards.

12 Claims, No Drawings

METHOD OF LOADING ORGANIC MATERIALS WITH GROUP III PLUS LANTHANIDE AND ACTINIDE ELEMENTS

STATEMENT REGARDING FEDERALLY SPONSORED RESEARCH OR DEVELOPMENT

This invention was made with government support under Contracts DE-AC05-84OR21400 and DE-AC05-96OR22464, awarded by the United States Department of Energy to Lockheed Martin Energy Systems, Inc., and Lockheed Martin Energy Research Corporation, and the United Sates Government has certain rights in this invention.

CROSS-REFERENCE TO RELATED APPLICATIONS

Not applicable.

BACKGROUND OF THE INVENTION

The present invention relates generally to a composition of matter comprising a tributylphosphate (TBP) complex of a salt of an element selected from the group consisting of group 3, lanthanide, actinide and group 13 elements, and an organic carrier. These materials may be used as scintillators, radiation absorption standards, and x-ray resonance fluorescence standards.

Determining the elemental composition of a sample material is an important objective in a variety of disciplines. Various approaches involving radiation may be used to determine the elemental composition of a material. In one method, a sample of unknown composition may be exposed to an x-ray beam, which causes it to fluoresce with the x-rays characteristic of its constituent elements. The abundances of the constituent elements may be determined by performing ab initio calculations of the response of the system as a function of the composition and physical characteristics of the sample. However, this approach is fairly complicated. A simpler, easier to use method of identifying and quantifying elemental constituents in an unknown sample involves comparing the measurement of x-rays emitted from the sample with measurements obtained from a series of standards of known composition and with physical characteristics similar to those of the sample. Although the latter method is easier to use than the former, it depends on the availabilty of accurate standards. Manufacture of such standards is often difficult.

The radiation absorption properties of materials are important in the fields of industrial and medical radiography, and dosimetry. Standards that mimic the absorption properties of the human body or manufactured articles are used to set exposure parameters of radiation generating equipment so that optimal images may be obtained.

Organic scintillators have been used to detect radiation for many years. Because they are formulated as solids or liquids, these scintillators are effective in detecting particulate radiation. However, these materials are made up largely of hydrocarbons (98%), which are relatively poor at detecting electromagnetic radiation; therefore, they are efficient detectors of only low energy (a few tens of keV) electromagnetic radiation. Although organic scintillators effective at detecting electromagnetic radiation of up to about 100 keV have been produced commercially using alkyl lead and tin additives, light output from the scintillator is greatly decreased by the presence of lead and tin.

What is needed in the art is a composition of matter that permits the easy, accurate, and rapid fabrication of radiation absorption standards to specified properties, and organic scintillators with enhanced sensitivity to electromagnetic radiation.

BRIEF DESCRIPTION OF THE SEVERAL VIEWS OF THE DRAWINGS

Not applicable.

BRIEF SUMMARY OF THE INVENTION

The present invention includes a composition of matter comprising a tributyl phosphate complex of a salt of an element selected from the group consisting of group 3, lanthanide, actinide, and group 13 elements and an organic solvent.

Another aspect of the present invention provides a method for making a composition of matter comprising a tributyl phosphate complex of a salt of an element selected from the group consisting of group 3, lanthanide, and actinide, and group 13 elements, and an organic solvent, the method comprising the steps of: combining the tributyl phosphate complex of a salt of an element, the element selected from the group consisting of group 3, lanthanide, actinide and group 13 elements, and a suitable carrier selected from the group consisting of an organic liquid carrier and an organic solid carrier precursor, under conditions that allow uniform dispersion of the complex in the carrier.

It is an object of the present invention to provide a composition of matter that may be useful as radiation absorption standards, as x-ray resonance fluorescence standards, or as organic scintillators with enhanced sensitivity to electromagnetic radiation.

It is a further object of the present invention to provide a material with specified radiation absorption characteristics that can conveniently be formulated in solid or liquid form.

It is an advantage of the present invention that tributylphosphate complexes of group 3, lanthanide, actinide, and group 13 salts can be incorporated in an organic solvent to form a clear liquid or solid material.

Another advantage of the present invention is that tributyl phosphate complexes of group 3, lanthanide, actinide and group 13 salts have a high solubility in organic solvents and in silicones, which allows loading of group 3, lanthanide, actinide or group 13 salts at relatively high concentrations.

Other objects, features, and advantages of the present invention will be apparent on review of the specification and claims.

DETAILED DESCRIPTION OF THE INVENTION

The present invention includes composition of matter comprising a tributyl phosphate (TBP) complex of a salt of an element selected from the group consisting of group 3, lanthanide, actinide and group 13 elements incorporated into an organic solvent or silicone liquid or in silicone rubber or a solid polymeric hydrocarbon matrix.

It is envisioned that the composition of the present invention may be modified or adapted for the fabrication of radiation absorption standards, fluorescence standards, or for purposes for which materials with specific radiation absorption characteristics are needed.

The present invention capitalizes on the discovery tributylphosphate complexes of nitrate salts of Group 3, lanthanide, actinide and group 13 elements are clear liquids that are miscible with phosphors in vinyltoluene and silicones. The resulting solutions can be polymerized to hard plastics or rubbers that retain the mechanical properties of the unadulterated material. Group 3, lanthanide, actinide and group 13 metals span the range of atomic numbers from 21 through 103 and offer the possibility of tailoring the x ray absorption properties of the loaded material.

The TBP complexes of group 3, lanthanide, actinide and group 13 metals, when added to organic scintillators, will enhance their efficiency in detecting gamma and x-rays. The usual formulation of organic scintillators includes only hydrocarbon carrier (plastic or liquid) and a small amount (<2%) of organic (primarily hydrocarbon) phosphors. These materials have very small photoelectric cross sections, which limits the range of incident energies for which spectral information can be obtained. The presence of even a small amount of an element with a relatively high atomic number, such as an actinide or a lanthanide, increases the probability of absorption of electromagnetic radiation via the photoelectric effect, thereby extending the range of incident incident energies for which an organic scintillator can provide spectral information. For example, the addition of 1% (w/w) Gd to an organic scintillator increases the photoelectric cross section by a factor of 22 at 60 keV and increases the ratio of photoelectric to Compton absorption by a factor of 14. This ratio and the photoelectric cross section determine what fraction of interactions in the scintillator contribute to peaks in the pulse height spectrum. TBP complexes of group 3, lanthanide, actinide, and group 13 metals can be used to load organic carriers with at least 1% (w/w) metal.

The TBP complexes have been demonstrated to have a high solubility in aromatic hydrocarbons and phenyl-substituted silicones, including, but not limited to, benzene, vinyl toluene, and similar liquids. Some of these organic liquids can be polymerized to form a solid. In most cases, the resulting liquid or solid takes on the color and optical clarity of the TBP complex. Materials made in this manner can form the basis or organic scintillators with enhanced gamma ray and/or neutron detection properties. In at least one case $(Eu(NO_3)_3TBP_3)$, the complex itself is phosphorescent and emits light in response to the absorption of radiation. Materials loaded with a group 3, lanthanide, actinide or group 13 element may also be used for x ray absorption standards by selecting either an optimum concentration of complex or selecting an optimum group 3, lanthanide, actinide, or group 13 element.

Incorporation of TBP complexes of spontaneously fissioning actinides into a solid or liquid organic scintillator offers a novel method of fabricating calibration standards for neutron detectors. When realized as a thin film or disk and coupled to a photosensor, fission events in the film or disk produce light flashes coincident with the emission of fission neutrons. By measuring the time of arrival of neutrons in a secondary detector relative to the light flash produced by the fission event, the energy of the neutrons and the response of the secondary detector as a function of neutron energy may be determined. Incorporating the actinide in the scintillator improves the physical stability of the actinide and the safety of subsequent encapsulation.

In addition, by using a block of scintillator, neutrons will be moderated in the block and by this means a source of slower neutrons (still with a light pulse indicating time of origination) can be fabricated. If it is desired to produce only slower neutrons by moderation, then the phosphors may be omitted from the organic solid or liquid.

The material of the present invention may be formulated as a liquid or solid by dissolving at least one tributyl phosphate-group 3, lanthanide, actinide, or group 13 salt complex in a suitable carrier. For scintillators, suitable liquid carriers for scintillators include, but are not limited to, aromatic hydrocarbon solvents and phenyl-substituted silicone liquids and suitable solid carriers include polyvinyltoluene, polystyrene, and phenyl-substituted silicone rubber. For other applications, the material may be formulated as a liquid by dissolving the TBP complex in a suitable organic solvent. A suitable organic solvent is one in which the TBP complex is soluble. Preferably, the solvent is a monomer capable of undergoing polymerization to form a more viscous liquid or a solid.

In the examples below, group 3, lanthanide, actinide, and group 13 elements were loaded in polyvinyltoluene or in phenyl-substituted silicone rubber. It is reasonably expected that any organic solvent or polymer in which the TBP complexes are soluble may be used in the practice of the present invention.

Preferably, a scintillator comprising the composition of matter of the present invention comprises at least one fluor or wave shifter. Examples of suitable fluors include, without limitation, 2,5-diphenyloxazole (PPO) or 2,5-bis(5-tert-butyl-2-benzoxazolyl) thiophene (BBOT). Additional fluros, such as 1,3,5-triphenyl pyrazoline and its derivatives, and coumarins, may be included to obtain scintillation at wavelengths above 420 nm. It should be appreciated that a fluor may be included in the scintillator alone or in combination with other fluors.

The scintillator of the present invention may be used to detect x-rays, gamma rays, or neutrons. When designed and fabricated to have absorption properties comparable to various types of human tissue, the scintillators of the present invention may be used in dosimetry studies to measure radiation exposure.

As described in the examples, the TBP complexes may be added to a carrier that conveniently is formulated to contain a fluor. One of skill in the art would appreciate that one wishing to practice the method of the invention could use a carrier that was not supplied with a fluor, and that the fluor could be added to the carrier. The order in which the various components are added is not believed to be critical.

The composition of the present invention may be cast during polymerization of the carrier precursor or machined after polymerization for use as x-ray absorption standard. The density of such standards may chosen to approximate that of the tissues affected by exposure to the x-rays (e.g., soft tissue or bone). The density of the standard may be adjusted by preselecting the type and concentration of TBP complex in the final composition.

The composition of the present invention may also be used in x-ray fluorescence standards in nondestructive testing. This may be accomplished by incorporating known amounts of an element, such as scandium, in a carrier to form a composition of known density. The sample, when exposed to a broad spectrum x-ray beam, will emit characteristic x-rays of scandium. If the standard is fabricated to have similar dimensions to those of actual specimens to be tested, then the absorption and scattering of scandium x-rays by the specimens will be duplicated by the standard and measurements of characteristic x-rays from the standard can be correlated to measurements of specimens. In this manner, an x-ray resonance fluorescence apparatus may be calibrated.

The complexes formed between tributylphosphate and the salts of group 3, lanthanide, actinide, and group 13 elements have high solubility in a variety of organic and silicone liquids. These tributylphosphate complexes may be used to prepare a solid composition by combining the complex with a solid carrier precursor in which the complex has a high solubility, such as a vinyl-substituted aromatic hydrocarbon or silicone rubber precursor. The tributylphosphate complexes disclosed in the examples do not interfere with polymerization, which may be accomplished by adding an initiator and heating to allow polymerization of the precursor to a solid.

The tributyl phosphate complexes used in the present invention do not absorb a significant amount of light in the visible or near-ultraviolet region of the spectrum, and liquid and solid compositions of the present invention remain optically clear. In addition, the tributylphosphate complexes used herein do not destroy or significantly quench the scintillating properties of fluor molecules, which may optionally be included in the composition. Measurements indicate that even levels of 30% (w/w) of the TBP complex in an organic liquid scintillator do not completely quench the fluor.

The following nonlimiting examples are intended to be purely illustrative.

EXAMPLES

Preparation of a Tributyl Phosphate Complex with a Group 3, Lanthnide, Actinide Salt or Group 13

A complex of tributylphosphate and a salt of a group 3, lanthanide, actinide, or group 13 element was prepared by contacting an excess of a solid salt (nitrate or salicylate) of a group 3, lanthanide, actinide, or group 13 element with liquid TBP. An excess of salt was agitated with TBP for 2 hr at ambient room temperature. The salt should be added in an amount sufficient to give an excess of the element over TBP relative to the ratio of the element to TBP in the desired TBP complex. If the stoichimetric ratio of metal:TBP :in the TBP complex is 1:3, the metal salt may be added at a ratio of 1 mole salt:2 moles of TBP. The salt could be added in an amount sufficient to saturate the TBP. The group 3, lanthanide, actinide or group 13 element and its associated anions were extracted into the TBP phase, thereby forming the desired TBP complex. Depending on the water content of the salts, the mixture may separate into organic and aqueous phases. To promote complete phase separation, the mixture may be centrifuged and the organic phase, which comprises the TBP complex, may be removed by pipetting. The TBP complex may be used in this form to prepare organic solvent based preparation. Because water has significant solubility in TBP, the water must be removed prior to use in the formation of silicone-based scintillators.

Using the above method, we have incorporated the following metals into TBP complexes: Eu, Ho, Tb, Gd, Dy, Yb, Y, and In. These complexes were found to have optical clarity, compatibility with organic fluors, are usually colorless, and are stable at temperatures of at least about 110° C.

Formation of TBP-complexes in a Liquid Carrier

A TBP complex prepared as described in the previous example may be directly combined with the carrier or carrier precursor. The TBP complexes are readily soluble in commercial liquid scintillators (such as Packard Insta-Gel XF) or pseudocumene-containing organic fluors. The complex may be added in an amount sufficient to give a final concentration of group 3, lanthanide, or actinide element of up to about 3% (w/w). The complexes were found to be readily soluble in phenyl-substituted silicone liquids. Optionally, the PPO and BBOT fluors may be added at a level of from about 0.1% to about 1.5%, depending on the solubility in the liquid carrier, to form a scintillator.

An organic liquid scintillator comprising up to about 30% (w/w) Gd nitrate TBP (3% Gd metal) was prepared and tested to determine its quenching characteristics. A 70% loss of light was observed at 3% Gd metal. It is expected that comparable levels of the other group 3, lanthanide, actinide, and group 13 metals could also be incorporated into organic materials and would result in materials that exhibit quenching characteristic comparable to Gd.

Formation of TBP Complex-containing Solid Carrier

Tributylphosphate complexes formed with salts of group 3, lanthanides, actinides or group 13 were dissolved in a monomer such as styrene or vinyltoluene containing the initiator benzoyl peroxide (0.8%) by agitating at room temperature. Optionally, for materials to be used as a scintillator, the monomer solution may also contain an organic fluor such as PPO (1.2–1.5%) or BBOT (0.1%) or both. The crosslinker divinylbenzene was added at a final concentration of 0.4–1.0%. Nitrogen gas was bubbled through the mixture for several minutes to remove dissolved and entrained $O_2$, and the mixture was centrifuged. The organic phase was removed from residual water that separates during centrifugation, and the mixture was placed in a container for polymerization. The mixture was further degassed by passing dry $N_2$ or Ar in the headspace to remove air. The mixture was placed in a vacuum oven (50 mm Hg) at 57° C. for 65 hr. The resulting solid was optically clear. The group 3-, lanthanide-, actinide-, and group 13-containing complexes are stable at temperatures needed for polymerization and do not degrade to form colored complexes that may interfere with organic fluors, which may be optionally included.

Preparation of Tributylphosphate Complexes in Silicone Precursor System

Tributylphosphate complexes were dissolved in two-component silicone precursor systems comprising a vinyl-terminated poly(dimethyl/diphenyl)siloxane and poly(methylhydro/methylphenvl)siloxane. Optionally, the precursors system may also contain PPO, BBOT, or both PPO and BBOT as organic fluors. To this mixture, initiators were added to the mixture to initiate polymerization. Either Gd(undecanoate)$_3$ or Gd (octanoate)$_3$ was first added to the mixture as a promoter. The mixture was heated to 110° C. to dissolve all the components in solution. The mixture was cooled to room temperature and degassed by a combination of centrifugation and evacuation. A commercially available xylene solution of a Pt vinyl complex (platinum (divinyl) (tetramethyldisiloxane) complex United Chemical Technologies, Inc.) was added as an initiator. The mixture was then centrifuged for a few minutes to remove entrained gas bubbles, followed by a brief evacuation to complete removal of gas. The reaction mixture was heated to a mild temperature (60° C.) for 4–8 h. The polymer thus formed is optically clear with good mechanical properties (e.g., no surface cracking or crazing).

The present invention is not limited to the exemplified embodiments, but is intended to encompass all such modifications and variations as come within the scope of the following claims.

We claim:

1. A single phase solid composition of matter comprising at least one tributyl phosphate complex of a salt of an element selected from the group consisting of group 3, lanthanides, actinides and group 13 elements intermixed with a polymer, wherein said solid composition is colorless.

2. The composition of claim 1, wherein the tributylphosphate complex comprises salicylate.

3. The composition of claim 1, wherein said polymer comprises at least one rubber.

4. A neutron source comprising at least one tributyl phosphate complex of a salt of an actinide element and an organic polymer in a single solid phase, the actinide element having the property of undergoing spontaneous fission.

5. The neutron source of claim 4, further comprising at least one fluor marker, said marker for indicating when neutrons are emitted from said neutron source.

6. A radiation absorption standard for detecting x-rays, gamma rays, or neutrons comprising at least one tributyl phosphate complex of a salt of an element selected from the group consisting of group 3, lanthanides, actinides, and group 13 elements, and an organic polymer, said radiation absorption standard being in a single solid phase.

7. The radiation absorption standard of claim 6, wherein said solid phase comprises at least one rubber.

8. A scintillator comprising at least one tributyl phosphate complex of a salt of an element selected from the group consisting of group 3, lanthanides, actinides, and group 13 elements, an organic polymer and at least one fluor, said scintillator being single phase and solid, said tributyl phosphate complex combined with said organic polymer being uncolored and substantially transparent to fluorescent light emitted by said fluor upon irradiation of said scintillator.

9. A method for preparing a composition of matter comprising at least one tributyl phosphate complex of a salt of an element selected from the group consisting of group 3, lanthanides, actinides and group 13 elements, at least one fluor, and an organic polymer comprising the step of:

(a) mixing a tributyl phosphate complex of a group 3, lanthanides, actinides, or group 13 salt complex and a solid carrier precursor, under conditions that allow uniform dispersion of the complex and the fluor in the carrier, and polymerizing said solid carrier precursor to form a polymer, said composition being solid, said tributyl phosphate complex combined with said polymer being uncolored and substantially transparent to fluorescent light emitted by said fluor upon irradiation.

10. The method of claim 9, wherein the carrier is a solid carrier precursor selected from the group consisting of styrene and vinyltoluene, further comprising the steps of:

(b) mixing an initiator and a crosslinker with the mixture of step (a);

(c) heating the mixture of step (b) to a suitable temperature for a period of time sufficient to allow polymerization to occur.

11. The method of claim 9, wherein the carrier is a precursor of phenyl-substituted silicone rubber, further comprising the steps of:

(b) mixing a Gd(carboxylate)$_3$ with the mixture of step (a) under suitable conditions to allow dissolution of the components; and (c) mixing an initiator with the solution of step (b) under conditions that allow polymerization to occur.

12. The method of claim 9, wherein said carrier is silicone.

* * * * *